(12) United States Patent
Shu

(10) Patent No.: US 8,337,907 B2
(45) Date of Patent: Dec. 25, 2012

(54) USE OF VOLATILE OIL FROM PLANTS IN PREPARING MEDICAMENTS FOR PREVENTING AND TREATING DIABETES

(76) Inventor: Gang Shu, Alhambra, CA (US)

( * ) Notice: Subject to any disclaimer, the term of this patent is extended or adjusted under 35 U.S.C. 154(b) by 299 days.

(21) Appl. No.: 12/660,318

(22) Filed: Feb. 24, 2010

(65) Prior Publication Data

US 2010/0272835 A1  Oct. 28, 2010

Related U.S. Application Data

(63) Continuation of application No. PCT/IB2008/002215, filed on Aug. 27, 2008.

(30) Foreign Application Priority Data

Aug. 27, 2007  (CN) .......................... 2007 1 0125948

(51) Int. Cl.
*A01N 65/00* (2009.01)
(52) U.S. Cl. ........................................................ 424/725
(58) Field of Classification Search .................. None
See application file for complete search history.

(56) References Cited

U.S. PATENT DOCUMENTS 4,083,994 A  4/1978 Noda et al.

FOREIGN PATENT DOCUMENTS

| CN | 2006100459198 | 9/2007 |
| CN | 2007100125948 | 3/2009 |
| DE | 19644422 A1 | 4/1998 |
| GB | 2111384 A | 7/1983 |
| WO | PCT/CN2007/000550 | 9/2007 |
| WO | PCT/IB2008/002215 | 4/2009 |

OTHER PUBLICATIONS

Wang Weijiang, Recent advances on limonene, a natural and active monoterpene, China Food Additives, 2005, No. 1, pp. 33-37.
Liu Jianhui et al., Separation and Identification of Primary Chemical Ingredients in Perilla oil. Flavour Fragrance Cosmetics, 1998, No. 1, p. 19-20,3.

*Primary Examiner* — Michael Meller

(57) ABSTRACT

The present invention provides the use of d-limonene as a monocyclic monoterphene in manufacturing medicaments for treatment of diabetes. Particularly the use of such compound in manufacturing medicaments for treatment of diabetes of type 1 or type 2 is provided.

1 Claim, No Drawings

USE OF VOLATILE OIL FROM PLANTS IN PREPARING MEDICAMENTS FOR PREVENTING AND TREATING DIABETES

TECHNICAL FIELD OF INVENTION

The present invention relates to compound d-limonene including its method of made in, and its applications of made in diabetes on type 1 and type 2 diabetes. The present invention relates to a medical indication of d-limonene, especially, relates to a new medical indication for pharmacy. Indeed, related to application of made in treatment diabetes.

BACKGROUND ART

Compound Limonene has been already disclosed by the State of Art and knowledge, its chemical name is Cyclohexene, 1-methyl-4-(1-methylethenyl)-, (+)-(R), or 1-methyl-4-prop-1-en-2-yl-cyclohexene. Molecular Formula is C10H16, a molecular weight of 136.32, it is a liquid which do not in water but in ethanol. Limonene consist of three optics isomers, d-limonene, l-limonene and dl-limonene.

d-limonene's chemical name is (4R)-1-methyl-4-prop-1-en-2-ylcyclohexene. It consist in oils extracted from the citrus rind, limon, bergamot, dill and orange, etc. Its boiling point is 178° C., 61° C. (1.60 kPa), Density is 0.8411.

l-limonene is little in the orange oils, it can to form by chemical synthesis from other aroma compounds. It consist in oils extracted from Russia turps, and cajeput, etc. Its boiling point is 177.6-177.8° C., 61° C. (100.7 kPa), Density is 0.8422.

dl-limonene consist in oils extracted from Siberian pine needle, Lemongrass, and vanilla, etc. its boiling point is 178° C., 64.4° C. (2.0 kPa). Density is 0.8402.

Anyone of tree above is oily liquid. To distill have not chemical change in normal press, but it can itself easily be oxidised to complex compounds as oxygenates and polymer, etc. their flash point is 48° C.

Molecular biological studies of drug's action show that the chiral drugs present stereoselectivity in its drug absorption, transport, distribution, metabolism, excretion in the body, and binding thim with targets including absorption, enzymes and ion channels, etc. Therefore, both pairs of enantiomer often show different characteristics of pharmacology, toxicology and different pharmacokinetic properties. In many cases, between pairs of the enantiomer of compound both have significant differences in pharmacological activity, metabolic processes, metabolic rate, and toxicity in the organism.

However, it is common sense to at least one of isomer with same feature when racemic has some feature, so that, we can think that dl-Limonene some pharmacological effects of d-limonene. Respectively, this compound Limonene is obtained from the volatile oil of following plants or herbs, using the Fractionation method.

Rutaceae Lemon (*Citrus limon* (L.) Burm. f.) and its cultivar of the fresh mellow fruit, pericarp and leaf. Or, Rutaceae orange (*Citrus reticulata* Blanco) and its cultivar of the fresh mellow pericarp or dried mellow pericarp (It is called pericarpium Citri Reticulatae in traditional Chinese medicine), or dried little fruit or dried green pericarp (It Is called pericarpium Citri Reticulatae Viride in traditional Chinese medicine). Or, Sweet Orange (*C. aurantium*) of the fresh mellow fruit, pericarp and seed. Or, Sour Orange (*Citrus aurantium*) of the fresh mellow pericarp. Or, Sour Orange (*Citrus aurantium*) and its cultivar or Sweet Orange (*C. aurantium*) of the dried green pericarp (It Is called Fructus Aurantii lmmaturus in traditional Chinese medicine). Or, Wasp Orange (*C. hystrix*) of the fresh mellow fruit and pericarp. Or, *Citrus Bergamia* (*C. bergamia*) of the fresh mellow fruit and pericarp. Or, Rutaceae Fingered Citron (*Citrus medica* L. Var *Sarcodactylis* Swingle) of the fresh green pericarp or dried pericarp. Or, Umbelliferae Rhizoma seu Padix Notopterygii (*Notopterygium incisum* Ting ex H. T. chang) or wide blade Umbelliferae Rhizoma seu Padix Notopterygii (*N. forbesii* Boiss) of the root-stock and root. Or, Zingiberaceae Ginger (*Zingiber officinale* (Willd) Rosc.) of the fresh root-stock. Or, *Perilla* Leaf (*Perilla frutescens* (L.) Britt.) of the root. Or, Magnoliaceae Yulan (M. denudate Desr. [*M. heptapeta* (Buch.) Dandy; *M. conspicua* Salisb; M. yulan Desr.]) or Yulan in Wudang (*M. sprengeri* Pamp.) of the dried bud (It is called Flos Magnoliae in traditional Chinese medicine). Or, Herba Schizonepetae (*Schizonepeta tenuifolia* Briq) of the portion found above ground. Or, Umbelliferae North Radix Bupleuri (*Bupleurum Chinense* DC.) or narrow leaf (*B. scorzonerifolium* Willd (*B. falcatum* L. var. *scorzonerifolium* Ledeb.)) of the dried root (It is called Radix Bupleuri in traditional Chinese medicine). Or Japanese *B. falcatum* L. (*B. scorzonerifolium* willd var *stenphyllum* Nakai) of the dried root. Or, Labiatae Herba Menthae [*Mentha haplocylyx* Briq. (*M. arvensis* L. var *haplocalyx* Briq.) and *Mentha haplocalyx* Briq. (Var *piperasoens* (Malinvand) C. Y. Wu et H. W. Li (*M. arvensis* L. var *piperascens* Malinvaud.))] of the herb. Or, Saururaceae *houttuynia cordata* (*Houttuynia cordata* Thunb) of the herb (It is called Herba Houttuyniae in traditional Chinese medicine). Or, Asteraceae Flos Chrysanthemi Indici (*Chrysanthemum indicum* L.) of the capitulum. Or, Piperaeeae *Piper kadsura* (*Piper kadsura* (choisy) Ohwi and *Piper walli chii* (Miq) Hand-Mass) of the dried rattan (It is called Caulis *Piper Kadsurae* in traditional Chinese medicine). Or, Labiatae Glechoma hederacea (Glechoma longituba (Nakai) Kupr.) of the portion found above ground (It is called Herba Glechomae in traditional Chinese medicine). Or, Rutaceae Pericarpium Zanthoxyli (*Zanthoxylum schinifolium* Sieb. Et Zucc.), or Pricklyash Peel (*Zanthoxylum bungeanum* Maxim), or *Zanthoxylum simulans* (*Z. simulans* Hance) of the dried mellow pericarp. Or, Umbelliferae Fennel (*Citrus aurantium* L.) of the dried mellow fruit (It is called Fructus Foeniculi in traditional Chinese medicine). Or, Rutaceae Sour Orange (*Citrus aurantium* L.) and its cultivar of the crude fruit (It is called Fructus Aurantii in traditional Chinese medicine). Or, Umbelliferae Caraway (*Carum carri* L.) of the fruit (It is called Fructus cari carvi in traditional Chinese medicine). Or, Chenopodiaceae Herba Chenopodii (*Chenopodium ambrosioides* L.) of the herb. Or, Compositae *Artemisia Vulgaris* (*Artemisia argyi* Le vl. et Vant.) of the dried leaf. Or, Gramineae *Cymbopogon distans* (*Cymbopogon Distans* (Nees) A. Camus) of the herb. Or, Pinaceae White Bark Pine (*Pinus bungeana* Zucc.) of the cones (It is called Strobilus Pini Bungeanae in traditional Chinese medicine). Or, Ericaceae Rhododendron lutescens (*Rhododendron anthopogonoides* Maxim.) of the herb. Or, Erigeron Breviscapus (*Erigeron breviscapus* (Vant.)Hand.-Mazz) of the dried herb (It is called Herba Erigeronis Breviscapi in traditional Chinese medicine). Or, Compositae *Artemisia Annua* (*Artemisia annua* L.) of the herb (It is called Herba Artemisiae Annuae in traditional Chinese medicine). Or, Rutaceae Garden Rue (*Ruta graveolens* L.) of the herb (It is called Herba Rutae in traditional Chinese medicine). Or, Luraceae Litsea Cubeba (*Litsea cubeba* (Lour.) Pers.) of the dried mellow fruit (It is called Fructus Litseae in traditional Chinese medicine). Or, Magnoliaceae Chinese Anise (Illicium verum Hook. f.) of the dried mellow fruit. Or, Compositae *Carpesium Abrotanoides* (*Carpesium abranoides* L.) of the dried mellow fruit (It is called Fructus Carpesii in traditional Chinese medicine). Or, Labiatae *Pogostemon cablin* (*Pogostemon cablin* (Blanco) Benth.) and *Agastache* (*Agastache rugosus* (Fisch. et Mey.) O. Ktze) of the herb. Or, Cyperaceae *Cyperus rotundas* (*Cyperus rotundus* L.) of the root-stock. Or, Burseraceae Myrrh (*Commiphora myrrha* Engl.) of the Resins from bark. Or, Zingiberaceae Cardamomum (*Amomum villosum* Lour.) and *Amomum xanthioides* (*A. villosum* Lour. Var xanthioides T. L. Wu et Senjen) and *Amomum longiligulare* (*A. longiligulare* T. L. Wu) of the dried mellow fruit (It is called Fructus Amomi in traditional Chinese medicine). Or, Labiatae *Perilla* Leaf (*Perilla frutescens*(L.)Britt.) of the dried leaf. Or, Valerianaceae *Valerian* (*Valerian officinalis* L.) and wide blade *Valerian* (*V. officinalis* L. var. *latifolia* Miq) of the root and root-stock. Or, Leguminosae Alfalfa (*Medicago Sadiva* L.) or *Medicago* polymorpha (*Medicago hispida* Guertn) of the herb. Or, Rutaceae *Acronychia* (*Acronychia pedunculata* (L) Miq) or Powell's pedunculata (*A. baueri*) of the leaf. Or, Labiate Mosla Scabra (*M. scabra*(Thunb.)C. Y. Wu et H. W. Li) of the herb. Or, Rutaceae Lemon basil (*Ocimum basilicum* var. *citriodorum*) of the leaf.

Plant essential oils also produce a large number of by-product when wiping out terpene from oils and distilling or making synthetic camphor.

Limonene is mainly used for enamel, lacquer and a variety of solvents of oil-resin, resin wax, metal drier, and used in the manufacture of synthetic resins and synthetic rubber. Used in food, detergent and other household essence, they can still artificial preparation of citrus oils for oral such as the orange flavor essence of the formula.

U.S. Pat. No. 4,083,994 published that d-limonene can be used as the active component of choleretic drugs. In addition, the toxicity experiments published by U.S. Pat. No. 4,083,994 showed that d-limonene has extremely low toxicity. d-limonene's high biological safety are suitable for oral use. when administered d-limonene to rats by orally, LD50 for 6.0 g/kg.

The state of art and knowledge published that part of the pharmacokinetic data of d-limonene. d-limonene is absorbed rapidly after oral administration from the gastrointestinal, and it is distributed to all parts of the body, 75-95% of the absorbed drug will excreted by the urethra within 48 hours. limonene is excreted mostly by the urethra, about 60% of the all is eliminated in the urine within 24 hours, 5% is eliminated in the dejecta, and 2% is eliminated in the $CO_2$ exhaled. Its primary metabolites are the Dihydrotestosterone acid *Perilla* and *Perilla* acid, convert from about 35% limonene of in plasma. After oral administration of limonene, *Perilla* acid methyl ester and Dihydrotestosterone *Perilla* acid methyl ester are measured in plasma, but there has 5% from initial limonene only. Another metabolite is limonene 1,2-diol, convert from about 18% limonene of the initial volume.

Diabetes is a complex disease characterized by hyperglycemia. The disease can be divided into two major subclasses: insulin-dependent diabetes mellitus (IDDM), also known as type I diabetes, and non-insulin-dependent diabetes mellitus (NIDDM), also known as type II diabetes. IDDM results from insulin deficiency caused by cell-mediated autoimmune destruction of pancreatic beta cells. (World Health Organization Study Group. Diabetes mellitus. WHO Tech. Rep. Ser. 844, 1994). Type 1 diabetes develops when the body's immune system destroys pancreatic beta cells, the only cells in the body that make the hormone insulin that regulates blood glucose. Type 1 diabetes may account for 5% to 10% of all diagnosed cases of diabetes.

Type 2 diabetes may account for about 90% to 95% of all diagnosed cases of diabetes. It usually begins as insulin resistance, a disorder in which the cells do not use insulin properly. As the need for insulin rises, the pancreas gradually loses its ability to produce insulin. (U.S. Department of Health and Human Services, CDC, National Diabetes Fact Sheet, 2003).

Both IDDM and NIDDM can cause macrovascular, microvascular and neuropathy complications. Diabetes can affect many parts of the body and can lead to serious complications such as blindness, kidney damage, and lower-limb amputations.

In 2003, the Centers for Disease Control and Prevent (CDC) of China estimated about 40 million people have diabetes in China. European Union estimates that about 22.5 million people have type 2 diabetes in Europe in 2005. 20.8 million people have diabetes in the United States in 2005. Estimated cost of diabetes in the United States, 2002 Total (direct and indirect) for $132 billion, Direct medical costs for $92 billion, Indirect costs for $40 billion (disability, work loss, premature mortality). The World Health Organization (WHO) estimates that more than 180 million people worldwide have diabetes in 2005.

Current, major drugs of treatment of type 2 diabetes have some following:

1. Biguanides, its effective is low, and have biggish side-effect, often cause lactic acidosis if use for long-term.
2. Sulfonylureas, its side-effect is bigger, and often occur hypoglycemia if use for long-term, and islets of Langerhans may occur tire or crock up, secrete function of endogenesis insulin farther reduce, the drugs may secondary failure.
3. Glucosidase inhibitors, It delay absorb of glucose on small intestine only, and reduce postprandial blood glucose levels. It can not activate release of insulin, and also can not change fasting insulin and C-peptide concentration level.
4. Alone use insulin to treatment of type 2 diabetes, or use drugs type 1-3 above combining insulin, secrete function of endogenesis insulin will bankrupt, final result in insulin dependence. (WHO Study Group, WHO Technical Report Series 844, 1994)

All drugs above can not reduce blood glucose levels steadily. At the same time, the patient will need gradually increase the dosage of these drugs. United Kingdom prospective diabetes study indicate that all drugs can not stop sostenuto rise of fasting plasma glucose levels, indicating failure of islet cell function. (United Kingdom Prospective Diabetes Study Group, United Kingdom Prospective Diabetes Study, 1977-1992)

The current stability of the drug is difficult to control the disease process, diabetes, so there is no known case of the world, cured diseases, diabetes medication will be for life.

Present, Pharmaceutical companies and scientists are looking for newer versions of older agents, which may be more effective and have fewer side effects as well as entirely new agents with different mechanisms of actions.

CONTENT OF INVENTION

Summary of the Invention

The purpose of this invention is to provide new use of d-limonene, that is new application in the pharmaceutical. This invention relates to use of d-limonene in manufacturing medicaments for treatment of diabetes, particularly use of d-limonene in manufacturing medicaments for drug of reduce blood glucose. d-limonene is different than other anti-diabetes drugs of conventional synthetic chemical compounds as Biguanides or Sulfonylureas or Glucosidase inhibitor. This novel anti-diabetes drug is oil-like liquid compounds extracted from natural plant.

d-limonene is in various essential oils, particularly is in oils of lemon, orange, lime, grapefruit and bergamot. d-limonene can be obtained from steam extraction of citrus peels of orange, lemon, lime, grapefruit and bergamot. Distillation of the oils produces technical grades of d-limonene of higher purity for 95-96% about. Or use commercial products.

d-form limonene can be commercially obtained from Jishui South Pharmic Oil Manufactory (Jishui, Jiangxi, China), or Florida Chemical Company (Lake Alfred, Fla. United States).

The Extract Method of Essential Oil and D-Limonene

The temperature is high when using distillation method, material easy produce polymeric response cause deterioration, therefore, general using cold pressing method. With Rutaceae Lemon (*Citrus limon* (L.) Burm. f.) of the fresh mellow pericarp, or Rutaceae orange (*Citrus reticulata* Blanco) and its cultivar of the fresh mellow pericarp, or Sweet Orange (*C. aurantium*) of the fresh mellow fruit, pericarp and seed, or Sour Orange (*Citrus aurantium*) of the fresh mellow pericarp, or Wasp Orange (*C. hystrix*) of the fresh mellow fruit and pericarp, or *Citrus Bergamia* (*C. bergamia*) of the fresh mellow fruit and pericarp, or Rutaceae Fingered Citron (*Citrus medica* L. Var *Sarcodactylis* Swingle) of the fresh mellow pericarp, tear into shreds, and cold pressing directly, and by centrifugal effect and filtration, to extract the essential oil.

Or with Rutaceae orange (*Citrus reticulata* Blanco) and its cultivar of the dried mellow pericarp (It is called pericarpium Citri Reticulatae in traditional Chinese medicine), or dried little fruit or dried green pericarp (It Is called pericarpium Citri Reticulatae Viride in traditional Chinese medicine). Or with Sour Orange (*Citrus aurantium*) and its cultivar or Sweet Orange (*C. aurantium*) of pericarp of the dried little fruit (It Is called Fructus Aurantii Immaturus in traditional Chinese medicine). Dried pericarp should to submerge in water for 3-4 hours, each pericarp plus 8 parts water.

Or, to extract oil from fruit directly. Collecting clearly fruit of the orange, citrus and lemon, and send into different oilgrindingmachine to extract oil. Primary technics is FMC and BOE technics. And there have especial oilgrindingmachine in some countries and region.

Terpene removal technology of essential oil, may separate to recover d-limonene when fractionating in boiling point 178° C., 61° C. (1.6 kPa). Or, recover from general method.

These cold pressed oil or essential oil generated from cold press method, its d-limonene for over 90%. More, aldehyde removal by distillation in NaOH or Carbon radical addition agent, d-limonene purity for 99.5%.

U.S. Pat. No. 4,083,994 published that toxicology animal test of d-limonene, toxicity of d-limonene is low. It showed that d-limonene's high biological safety as oral agent.

The present invent first discovered in clinic that traditional Chinese medicine Rhizoma seu Padix Notopterygii or pericarpium Citri Reticulatae have clear effect of reduce blood glucose of type 2 diabetic patient. Farther study become conscious of that lemon or pericarpium Citri Reticulatae oil have more strong effect of reduce blood glucose. Finally, find that thereof pharmacological active ingredient is optics isomers d-limonene of the compound limonene.

In animal test of the present invent, this agent shown that has clear effect of reduce blood glucose for drug-induced diabetic rats. Oral administration of d-limonene (0.8-2.4 ml/kg) to experimental animal, and within 0.5-2 hours, blood glucose level reduce a lot, drug action graduate away after 2 hours of oral administration.

The present invent can reduce fasting blood glucose of that severe case streptozotocin-induced rats of type 1 and type 2 diabetes. Diabetic rats were intubated with d-limonene (0.8-2.4 ml/kg body weight with drug), after 0.5-2 hours, blood glucose of experiment rats clear reduce down. And, d-limonene do not reduce blood glucose of healthy rats.

Unhoped-for, d-limonene no only reduce blood glucose of the type 2 diabetes but also reduce blood glucose. One interpretation would is that the drug have different mechanism to influence secrete of the insulin than other agents.

In clinic test, a little patients of type 2 diabetes were oral administration of d-limonene for 0.9 ml after three meals daily, result shown that the drug can clear and stably reduce postprandial blood glucose levels. Have not any clear sideeffect. And, the drug moved time of hysteretic peak glucose after oral, clew diabetes will are cured by the agent.

d-limonene shown that another especial properties in animal and clinic tests. increasing the dose does not more reduce blood glucose after reached effective dose, and does not appear hypoglycemia after high blood glucose. on the contrary, along with time lengthen of treat, hypoglycemia respond of the diabetic patients decrease or loss.

The results of animal test and clinic test shown that the invention related to a new use of compound d-limonene, it may be develop a novel anti-diabetes drug. In addition, it is drug of non-chemical synthesis from natural plants, it consist in human food chain formed since millions of years, the toxicity is very low.

The present invention may be one or acceptable multiple carrier by pharmacy, is conventional carrier-mediated as water, amylum, fibrin, glutin, agar, β-dextrin, fabaceous Lecithin or lecithin, etc. Compound d-limonene is administered as in the form of oral and injecting. When oral administration, optimal dosage form is troche, coating tablet, grain, capsule, suppository and inject liquid. usual dose of d-limonene is determined by the chosen route, by state of an illness, by the type of diabetes and more in this invention. Daily dose is 1.5-4.5 ml, optimal daily dose is 2.4-3.0 ml. three meal daily, take it three times a day. Or dose times as meals. Oral administration of drug within 1-10 minutes from take food into mouth.

Side effect is light dry mouth, Dizziness, fatigue, palpitations, constipation, cold sore, etc. response above will disappear when stop administration of drug or reduce dose. Healthy take d-limonene do not reduce postprandial or fasting blood glucose level.

DETAIL EXAMPLE

Follow will description of some examples of the present invention, but the content of invention not limited to.

Particular Specification of Invention

Example 1

Extract essential oil from fresh or dry pericarp above, and extract d-limonene from oils:

Tear up Rutaceae Lemon (*Citrus limon* (L.) Burm. f.) of the fresh mellow pericarp, send presser to cold press, or take Rutaceae orange (*Citrus reticulata* Blanco) and its cultivar of the fresh mellow pericarp or dried mellow pericarp (It is called pericarpium Citri Reticulatae in traditional Chinese medicine), one pericarp add 8 water, marinating for 3-4 hours.

1. Marinating

To dip pericarp in lime water of 1.5-3.0% for 6-10 hours, maintaining the PH value of 10-14, and the ratio of pericarp to lime water is 1 to 4-6. To peel sclerosis suitable for pressed. To use also sodium bisulfate, sodium carbonate, sodium sulfate and more for marinating except lime water.

2. Cleanout

To take pericarp to clean water for remove lime water and impurity.

3. Pressing

To extract the essential oils from the peel use presser.

4. Filtration or Separation

Mixture of oil and water issued from cold press or presser, accompany with a lot of peel, have uncertain viscosity. So that, need to filtrate and deposit time after time for reducing press of centrifugal machine. The peel filtrated can be recovered oil via alembic.

5. Centrifugation

The separation of oil and water is separating oil and water via use high speed oil-water separator. After separation, should let machine racing for 2-3 minutes, and with a lot of water to fly out oil remained. For pushing oil separate out from oil latex, may add 2% sodium hydroxide and little sodium sulfate into water of used press oil.

6. Refining and Dewaxing

Turbid gently crude essential oil, with Anhydrous sodium sulfate to dehydrate, later, filtered residue after standing clear and transparent, and centrifuging. Turbid crude essential oil, first standing clear and transparent, second with Anhydrous sodium sulfate to dehydrate, final centrifuging.

To place crude essential oil in low temperature to standing, separate out waxiness, remove it use centrifuge method need 6 hours under conditions of 8° C., or need 2 hours under conditions of −25° C. There can obtain d-limonene of pure over 90% from pericarp of lemon, and obtain d-limonene of pure for 80-90% from orange peel.

7. Purification d-limonene obtained by cold press, can be fractionated use distillation in boiling point 178° C., 61° C. (1.60 kPa), to receive d-limonene of pure for 99%. More distil in dilute NaOH or Carbon based addition agent (hydroxylamine chlorohydrate) to remove aldehyde, its pure maybe for 99.5%. But, d-limonene sublimated will feedback with oxygen in air to translate into crude d-limonene of pure for 95-96% if do not give it any protect.

Example 2

Make essential oil d-limonene process into oral administration of tablet or injecta:

essential oil mix with some β-dextrin by spray, and add water, mix round for one hour in determinate temperature, and place cold storage for 24 hours, filtrate and take out, add a little of aether wash in twice, dry become powder under conditions of 50° C. And add enough water again, to reclaim essential oil, account callback rate.

the ratio of essential oil to β-dextrin is 1 to 9 (ml:g), mix round speed is 100 r/min, inclusion temperature is 40° C., the ratio of β-dextrin to water is 1 to 7, its essential oil callback rate is 88.0%. Or, take 25 g Fabaceous Lecithin add into distilled water, mix round thrice in emulsification machine, per time for 3 minute. and add 500 ml d-limonene, mix oil with water fully. And mix with β-dextrin, make tablet.

Or, filtrate oil-water mix liquid, that is sealed after filling, sterilize for 30 minutes under conditions of 100° C., made of ampoule.

Example 3

The Test of Type 2 Diabetes of Rat Model

Establishment of a type 2 diabetes rat test model. Use fast-generated model as of NIDDM. Once enough dose streptozotocin (STZ) administration of test animal Wistar rats, cause damage of a lot of β-cells, and synthesize and excrete of insulin, arose foul-up of sugar metabolism, lead to diabetes. streptozotocin (STZ) was dissolved in 0.1 mol/L asepsis sodium citrate buffer solution, to form a liquid for 2%, to adjust value PH to 4.5, use a bacteria filter to filter bacterial. After fasting for 18 hours to rats, form 60-65 mg/kg weight solution, the solution of the form 60-65 mg/kg weight was injected in a vein of tail. after 24 hours, Rats of blood glucose for 16.7 mmol/L as successful model. The fast-generated model often do not occur phenomena of self-catabatic when single dose for 50 mg/kg, 6-27 days, Islet have some rebirth, part of function renew, but have not back to natural, still at high blood glucose tide, for correlation research of the NIDDM.

After streptozotocin (STZ) is injected for 10 hours, oral administration of 10% glucose liquid to rats for prevent hypoglycemia.

In related to the testing, streptozotocin (STZ) was dissolved in 0.1M citric acid-trisodium citrate dihydrate buffer (pH 4.2) to form 60-65 mg/kg weight solution, and the solution was injected in a vein of tail immediately. Ten days later, after verifying that blood sugar level was sufficiently high, the test material was administered for 7 days, blood was taken from the animal was obtained using a normal method. A glucose monitoring system SureStep Meter of Johnson & Johnson Company was utilized for measurement of blood glucose levels.

In related to the feeding method, Wistar-type, seven-week-old male rats (weight 210.+−0.10 g), ten per group were used. Rats were fed under conditions of 22.degree. C. room temperature, 50% humidity and light-dark cycle of 12 hours (7:00.about.19:00). The drinking water was made freely available to the animals. Fasting for 4 hours, rats were intubated with d-limonene 0, and 2.4 ml/kg body weight with drug. After 2 hours, blood was taken from vein of tail of rats was obtained, check blood glucose level of experiment rats.

Test result as table 1 shown that P<0.01, have very marked difference, and curative effect very distinctness. Display drug d-limonene can reduce fasting blood glucose of type 2 diabetes rat model clearly.

TABLE 1

Compared before treat with after treat to type 2 diabetes rat model ($\bar{x} \pm S$)

| | Animal count | fasting glucose | Drug (ml/kg) |
|---|---|---|---|
| Before treatment | 10 | 27.14 ± 1.154 | |
| After treatment | 10 | 19.39 ± 6.064 | d-limonene 2.4 |
| t | | 3.970 | |
| p | | <0.01 | |

Example 4

The Test of Type 1 Diabetes of Rat Model

Establishment of a type 1 diabetes rat test model. Recent years, more people have definitely expressed that viewed streptozotocin-induced of diabetes test model. Although, it is a model of type 1 diabetes in principle, but can using as a model of type 2 diabetes. In any case, treptozotocin-induced of diabetic rat as type 1 diabetes of dependence of insulin when 1-6 day from be taken bad, so that, streptozotocin-induced of diabetic rat is rat model of type 1 diabetes during this period. streptozotocin-induced of diabetic rats were used, during 3-6 day from day of injecting streptozotocin, after fasting for 4 hours every day, diabetic rats were intubated with d-limonene 2.4 ml/kg body weight with drug, after 2 hours, blood was taken from vein of tail of rats was obtained, check blood glucose level of experiment rats. Result see table 2 shown that d-limonene treatment of type 1 diabetes of model rats, curative effect is marked.

TABLE 2

Compared blood glucose level of IDDM group with treat of d-limonene ($\bar{x} \pm S$)

| Group | Animal Count | Blood glucose (mmol/l) | | | | |
|---|---|---|---|---|---|---|
| | | First day | Second day | Third day | Four day | 1-4 days Average |
| IDDM | 12 | 25.27 ± 2.632 | 27.36 ± 1.243 | 26.08 ± 3.896 | 25.97 ± 2.966 | 26.17 ± 2.858 |
| Treat | 12 | 20.26 ± 5.039 | 22.08 ± 5.421 | 21.88 ± 5.754 | 23.32 ± 4.891 | 21.89 ± 5.230 |
| t | | 3.053 | 3.288 | 2.327 | 1.605 | 2.488 |
| p | | <0.01 | <0.01 | <0.05 | >0.05 | <0.05 |

Example 5

Streptozotocin-Indeced of Type 1 Diabetes Rat Model

Streptozotocin can selectivity damage β-cells of pancreatic islets, cause experimental diabetes. Rats were injected streptozotocin, follow change of blood glucose level appear tree phases: ① early high blood glucose phase, continuing for 1-2 hours about. Reason is the drug restrained release of insulin. ② low blood glucose phase, continuing for 6-10 hours. May be β-cells of pancreatic islets were destroyed, induce release of lot of insulin, so blood glucose reduce evidently. ③ Appeared steady-going high blood glucose phase after 24 hours, namely diabetes phase. Mostly of all β-cells presented different damage and destroy here. Streptozotocin-induced of high blood glucose of diabetes, its feedback and ketosis is relax than AlloXan-induced of diabetes.

Complete freund's adjuvant (CFA) and incomplete freund's adjuvant (IFA) have a character which inspire immunity function of body. Use small dose of streptozotocin with CFA, IFA, can activate lymphocyte of rat body, and induce β-cells occur light change. On the base, lymphocyte was activated so has cellular toxicity effect, it will attack cells of light change as target cell, thereby cause occur autoimmunity process, damage of β-cells farther develop, lead to diabetes.

Use continue inject CFA and IFA of method, once per week, continue 3 weeks, 0.5 ml CFA and IFA with 25 mg/kg STZ per time, Establishing delayed type diabetic Wistar rat model. Establishment of delayed type diabetic Wistar rat model, one mechanism would is that after inject CFA, lymphocyte of rat was activated, and small dose STZ induced β-cells occur light change, on the base above, T-lymphocyte activated of from spleen cells which has cellular toxicity effect, attack β-cells of light metamorphic as target cell, thereby cause occur autoimmunity process, damage of β-cells farther develop, lead to diabetes. Autoimmunity effect above was continue strengthened, cause damage of β-cells from quantitative change to qualitative change, final induced diabetes of rat.

Rats take food and drink in gear. first day, inject 0.5 ml CFA into abdomen, second day, inject STZ with 2.4 ml/kg body weight with drug. Second week, first day, inject 0.5 ml CFA into abdomen, second day, inject STZ with 2.4 ml/kg body weight with drug. Third week, first day, inject 0.5 ml CFA into abdomen, second day, inject STZ with 2.4 ml/kg body weight with drug. Continue three weeks. The delayed type STZ animal model has change of immunological, more approach arises, develop and change of IDDM of human.

After fasting 4 hours daily, diabetic rats were intubated with d-limonene 2.4 ml/kg body weight with drug, after 2 hours, blood was taken from vein of tail of rats was obtained, check blood glucose level of experiment rats. Result see table 2 shown that d-limonene treatment of type 1 diabetes of model rats, curative effect is marked.

TABLE 3

Compared before treating with after treating of type 1 diabetes ($\bar{x} \pm S$)

| | Animal Count | fasting glucose | Drug (ml/kg) |
|---|---|---|---|
| Before treating | 11 | 24.4 ± 2.958 | |
| After treating | 11 | 17.45 ± 1.886 | d-limonene 0.8 |
| t | | 6.575 | |
| p | | <0.01 | |

Example 6

Patient, male, 56 years old, type 2 diabetes for 10 years, fasting blood glucose was in normal state, postprandial blood glucose under 15.6 mmol/L (281 mg/dl). After meal for 4-6 hours, often occur hypoglycemic reaction if have not take food. A treatment of diabetes for 7 days, daily three meals, oral administration of d-limonene for 0.9 ml within 5-10 minutes from food into mouth, at breakfast, postprandial blood glucose peak for 11.8 mmol/L (212 mg/dl) in 1.25 hour of postprandial. Continuing treat for 12 weeks, the peak value for 10.4 mmol/L (212 mg/dl) and peak value time was moved forward to the meal of 0.75 hour. Sometimes, at supper, postprandial blood glucose for normal state without any drug was administered. At lunch, postprandial blood glucose for normal state or over normal level for a little without drug was administered. At breakfast, still can not stop oral administration of drugs. After the meal 6-8 hours, have not take food and have not hypoglycemic reaction. Patient keep measurable middling food and drink in the interim.

Example 7

Patient, feme, 58 years old, type 2 diabetes for 15 years, fasting blood glucose for 8.6-13 mmol/L (155-234 mg/dl), postprandial blood glucose maximum was 23 mmol/L (414 mg/dl). A treatment of diabetes for 7 days, daily three meals, oral administration of d-limonene for 0.9 ml within 5-10 minutes from food into mouth, at breakfast, postprandial blood glucose peak for 18.7 mmol/L (337 mg/dl) in 1.25 hour of postprandial. Compare before to after treating, blood glucose level average reduce 6.99 mmol/L (126 mg/dl). Patient keep measurable middling food and drink in the interim.

Example 8

Test to Healthy Volunteers

A man, 24 years old, Healthy have not any disease. Fasting blood glucose was waved in 4.4-5.3 mmol/L (79-96 mg/dl), A treatment of diabetes for 7 days, daily three meals, oral administration of d-limonene for 0.9 ml within 5-10 minutes from food into mouth, at breakfast, postprandial blood glucose peak for 6.3-8.4 mmol/L (115-150 mg/dl) in 0.5 hour of postprandial. Compared before and after treatment, blood glucose basically unchanged. Patient keep measurable middling food and drink in the interim.

Example 9

Test to Healthy volunteers

A woman, 46 years old, healthy without any disease. fasting blood glucose was waved in 5.0-5.4 mmol/L (79-96 mg/dl), in postprandial blood glucose 8-12.2 mmol/L (144-202 mg/dl) between. Abnormal glucose tolerance test. A treatment of diabetes for 7 days, daily three meals, oral administration of d-limonene for 0.9 ml within 5-10 minutes from food into mouth, at breakfast, postprandial blood glucose peak for 10.3-11.7 mmol/L (185-211 mg/dl) in 0.5 hour of postprandial. Compared before and after treatment, blood glucose basically unchanged. Patient keep measurable middling food and drink in the interim.

INDUSTRIAL APPLICABILITY

Raw material of Monoterpene compound limonene from Rutaceae Lemon (*Citrus limon* (L.) Burm. f.) and its cultivar of the fresh mellow fruit, pericarp and leaf. Or, Rutaceae orange (*Citrus reticulata* Blanco) and its cultivar of the fresh mellow pericarp or dried mellow pericarp (It is called pericarpium Citri Reticulatae in traditional Chinese medicine), or dried little fruit or dried green pericarp (It Is called pericarpium Citri Reticulatae Viride in traditional Chinese medicine). Or, Sweet Orange (*C. aurantium*) of the fresh mellow fruit, pericarp and seed. Or, Sour Orange (*Citrus aurantium*) of the fresh mellow pericarp. Or, Sour Orange (*Citrus aurantium*) and its cultivar or Sweet Orange (*C. aurantium*) of the dried green pericarp (It Is called Fructus Aurantii Immaturus in traditional Chinese medicine). Or, Wasp Orange (*C. hystrix*) of the fresh mellow fruit and pericarp. Or, Citrus Bergamia (*C. bergamia*) of the fresh mellow fruit and pericarp. Or, Rutaceae Fingered Citron (*Citrus medica* L. Var *Sarcodactylis* Swingle) of the fresh green pericarp or dried pericarp. Sources of raw materials is rich and extensive, output is very high. And, the compound can extract from essential oil of more for about 80 plants.

Origin from Europe, Asia, Africa, Australia, North America and South America. Thereof has the highest yield in Brazil of South America, and Florida of the United States, followed is Australia and South Africa. Raw materials worldwide, low price.

Second, the extraction method of d-limonene is easy. The most simple method is cold press, to receive orange oil or lemon oil of that d-limonene content for 80-90%.

Mix d-limonene with water by use of high-shear emulsifier, to made of injection. Or add into β-dextrin to made of troche, or add β-dextrin by spray to made of troche, or crank out of Soft Capsule directly. So that, for industrialization manufacture.

The invention claimed is:
1. A method of treating diabetes in a patient in need thereof consisting essentially of administering to the patient therapeutically effective amounts of d-limonene, *citrus limon, citrus reticulate blanco, citrus aurantium, fructus aurantii immaturus, fructus citri sarcodactylis, rhizoma seu Padix Notoptergygii* and *folium perillae* wherein said diabetes is treated in said patient.

* * * * *